United States Patent [19]
Agee et al.

[11] Patent Number: 5,924,999
[45] Date of Patent: Jul. 20, 1999

[54] METHOD AND APPARATUS FOR MONITORING AND IDENTIFYING SOUNDS CHARACTERISTIC OF TENDON TRANSLATION WITHIN THE CARPAL TUNNEL

[75] Inventors: John M. Agee, 3700 Toronto Rd., Cameron Park, Calif. 95682; Timothy R. Maher, Orangevale, Calif.

[73] Assignee: John M. Agee, Sacramento, Calif.; Trustee of the John M. Agee Trust dated August 15, 1996.

[21] Appl. No.: 08/740,777

[22] Filed: Nov. 1, 1996

Related U.S. Application Data

[60] Provisional application No. 60/007,221, Nov. 3, 1995, and provisional application No. 60/008,238, Dec. 6, 1995.

[51] Int. Cl.$^6$ .................................................. A61B 5/103
[52] U.S. Cl. ............................................ 600/587; 600/595
[58] Field of Search .................................. 600/561, 546, 600/587, 559, 552

[56] References Cited

U.S. PATENT DOCUMENTS

| | | | |
|---|---|---|---|
| 4,622,013 | 11/1986 | Cerchio | 434/118 |
| 4,807,642 | 2/1989 | Brown | 128/733 |
| 4,991,581 | 2/1991 | Andries | 128/715 |
| 5,010,889 | 4/1991 | Bredesen et al. | 128/715 |
| 5,010,890 | 4/1991 | Pfohl et al. | 128/773 |
| 5,022,405 | 6/1991 | Hok et al. | 128/715 |
| 5,027,825 | 7/1991 | Phelph, Sr. et al. | 128/715 |
| 5,035,247 | 7/1991 | Heimann | 128/715 |
| 5,129,403 | 7/1992 | Henriquez et al. | 128/773 |
| 5,301,679 | 4/1994 | Taylor | 128/773 |
| 5,305,238 | 4/1994 | Starr, III et al. | 364/569 |
| 5,462,065 | 10/1995 | Cusimano | 600/595 |
| 5,713,370 | 2/1998 | Cook | 600/595 |
| 5,715,834 | 2/1998 | Bergamasco et al. | 600/595 |

OTHER PUBLICATIONS

H.M. Büyruk, et al. *Colour Doppler Ultrasound Examination of Hand Tendon Pathologies* The Journal of Hand Surgery, vol. 21B, No. 4, Aug. 1996 pp. 469–473.

Bulent S. Cigali, et al. *Measurement of Tendon Excursion Velocity With Colour Doppler Imaging: A Preliminary Study On Flexor Pollicis Longus Muscle*, European Journal of Radiology 23 (1996) pp. 217–221.

Nakamichi, K., et al., "Restricted Motion of the Median Nerve in Carpal Tunnel Syndrome", From the Department of Orthopaedic Surgery, Toranomon Hospital, Minato–ku, Tokyo, Japan, Journal of Hand Surgery (British and European Volume, 1995) 20B: 4; 460–464.

Nakamichi, K., et al., "Transverse Sliding of the Median Nerve Beneath The Flexor Retinaculum", From the Department of Orthopaedic Surgery, Toranomon Hospital, Tokyo, Japan, Journal of Hand Surgery (British Volume, 1992) 17B: 213–216.

Robert E. Markisan, Treatment of Musical Hands: Redesign of the Interface, in Hand Clinics, pp. 525–544, vol. 6, No. 3, Pub. by W.B. Saunders Co., Aug. 1990.

*Primary Examiner*—Max Hindenburg
*Assistant Examiner*—Pamela L. Wingood
*Attorney, Agent, or Firm*—Morrison & Foerster LLP

[57] ABSTRACT

An apparatus and method for monitoring the energy, such as acoustic energy, generated by the translational (or "snapping") movement of tendons across the carpal tunnel, whereby an energy signature for such movement can be recognized. Feedback can then be provided to or about the person being monitored to permit, encourage, or force that person to choose a different movement whereby detrimental translational movement of tendons is reduced or minimized. Such reductions may result in a lower occurrence of CTS or the avoidance of its deleterious effects.

30 Claims, 3 Drawing Sheets

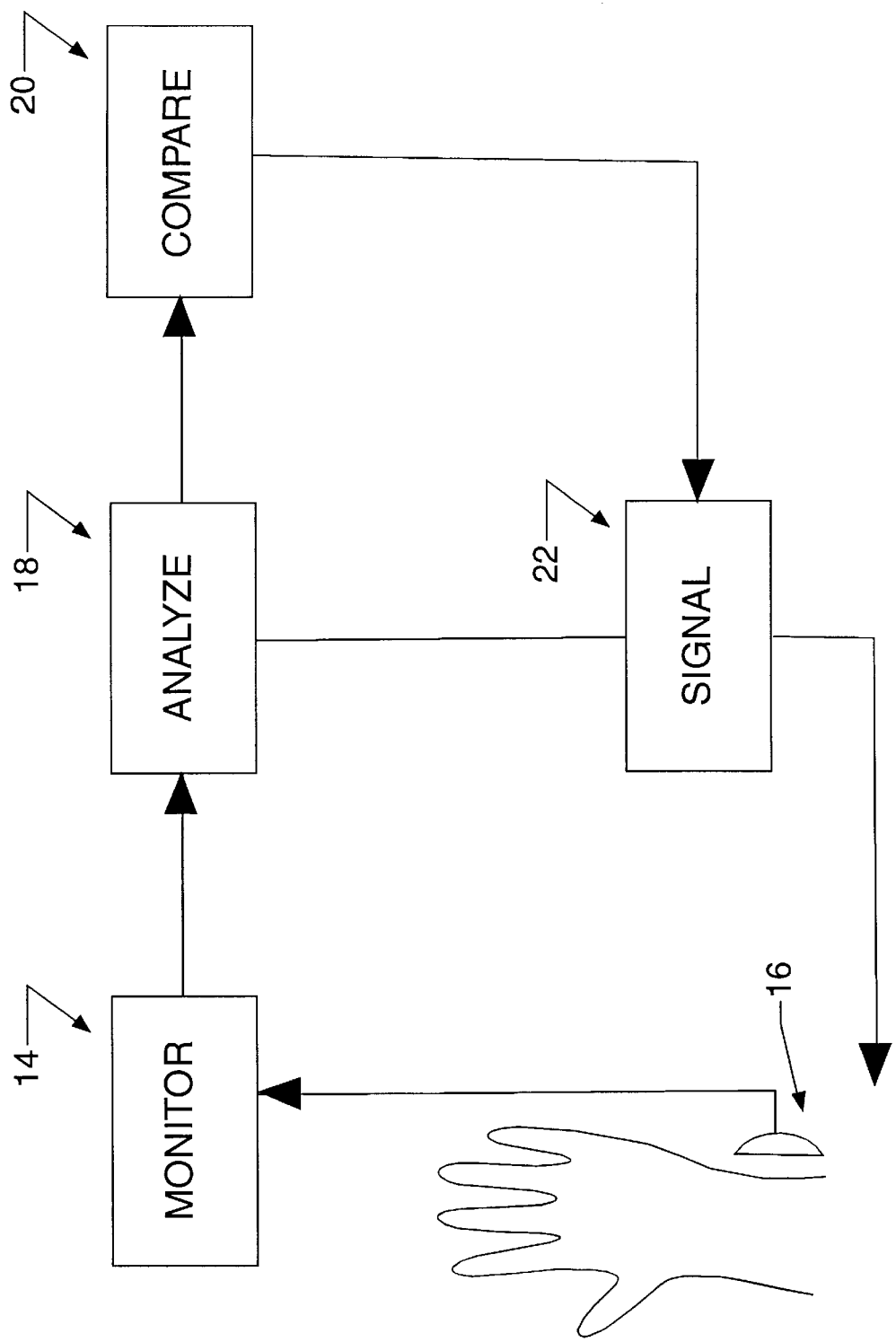

METHOD AND APPARATUS FOR MONITORING AND IDENTIFYING SOUNDS CHARACTERISTIC OF TENDON TRANSLATION WITHIN THE CARPAL TUNNEL

RELATED APPLICATIONS

This application claims the benefit of U.S. Provisional Application No. 60/007,221 filed Nov. 3, 1995 and Application No. 60/008,238, filed Dec. 6, 1995.

FIELD OF THE INVENTION

This invention relates a method and apparatus which can be used to identify signals characteristic of specific motions during relative movement of the carpal (wrist) contents, including the tendon, ligaments, synovium, cartilage and bones. More specifically, the invention relates to methods and apparatus which can identify signatures, such as acoustic signatures, within the carpal area, whereby dynamic, real-time, monitoring of these signatures can be used to reduce or prevent the incidence of so called "idiopathic" carpal tunnel syndrome.

BACKGROUND OF THE INVENTION

Carpal tunnel syndrome is at present the most widespread occupational health hazard in the industrial world. Many billions of dollars are being consumed each year in lost working time and in the diagnosis and treatment of this syndrome.

Although some of the physiological factors associated with idiopathic carpal tunnel syndrome are well documented, including a non-inflammatory increase in the volume of synovium resulting in an increase of pressure in the carpal tunnel contents, the etiology of the change in quantity of the synovium has remained obscure.

Tendons in general have high longitudinal strength and rigidity, but are soft compliant tissues in the transverse direction, much like a bundle of fine wires, which can be easily molded to different cross-sectional shapes, even under tension longitudinally. A synovium wraps around, nourishes and lubricates the nine tendons of the extrinsic muscle tendon units which pass through the carpal tunnel. Each finger of the hand utilizes two of these nine tendons, with the thumb utilizing the last, to flex the joints of the digits. The median nerve also passes through the carpal tunnel to enervate certain muscles and provide sensation to related areas of the hand. Any increase in volume of the carpal tunnel contents, either synovium or tendons, results in compression of this nerve with secondary signs and symptoms of carpal tunnel syndrome.

In anatomic areas other than the carpal tunnel the biomechanical effect of each tendon is defined by discrete fiberosseous tunnels, effectively forming pulleys, that dictate the precise offset and location of the tendon as it crosses the joint to generate the rotational forces or moments needed to effect controlled angulation and stability of each joint. A pulley with a precise moment arm is also required in the carpal tunnel for each tendon as it crosses the carpus. Due to the compliant nature of the synovium, these pulleys can only be formed and maintained in the carpal tunnel, for all motions of the carpus, by a synergistic tensioning of all nine tendons of the carpal tunnel to form "dynamic soft tissue pulleys" for each tendon. Without this dynamic action, a singular contraction of a muscle tendon unit would cause that tendon to translate past the unresisting tendons in a snapping action until it rested against the more rigid wall of the carpal tunnel. The moment arm required for precise control would be lost for that particular motion. Such singular contractions can occur in individuals using repetitive motions such as typing, knitting, or peeling of vegetables.

The brain normally orchestrates the simultaneous activation of all the proper muscle tendon units, but with continued, often boring or tiring, repetitive motions will economize or neglect to synergistically contract the needed muscle tendon units requisite to stabilize the tendon or tendons actually doing the work.

Normal synovium is a filmy, compliant tissue which is incapable of resisting any translational repositioning of the tendons. In the presence of unstable carpal tunnel tendons, the synovium is subjected to repetitive shear and other stresses that result in its thickening and loss of elastic compliance. The thickening which occurs over time, increases the pressure in the limited volume of the carpal tunnel, with the secondary compromise of the blood supply to the median nerve and secondary symptoms of carpal tunnel syndrome.

There has not heretofore been provided a method or apparatus to monitor the motions of the tendons in the carpal tunnel and distinguish whether they are sliding properly in "soft tissue pulleys" or are snapping past each other in such a way as to injure the synovium and predispose the individual to the occurrence of carpal tunnel syndrome.

SUMMARY OF THE INVENTION

This invention provides an apparatus and method for monitoring the energy, such as acoustic energy, generated by the translational (or "snapping") movement of tendons across the carpal tunnel, whereby an energy signature for such movement can be recognized. Feedback can then be provided to or about the person being monitored to permit, encourage, or force that person to choose a different movement whereby detrimental translational movement of tendons is reduced or minimized. Such reductions may result in a lower occurrence of CTS or the avoidance of its deleterious effects.

In one form of the apparatus, sensor means are used (either implantable within the wrist area or positioned over the skin in the wrist or hand area (or other areas of the body acoustically linked to the carpal area)) for monitoring energy generated in the wrist region due to tendon translation. The apparatus may further comprise means for providing information gathered by the monitor means to a person or to a computer, such that the information may be compared with previously obtained and stored data. Additionally, the apparatus may comprise means for providing feedback to or about the person on whom the sensor means have been placed to promote or encourage movements which limit tendon translation or tendon snapping. Thus, the feedback provided by the apparatus to the user may be passive, i.e. simply informational, or it may be active, i.e. preventing operation of equipment if the user's hand use patterns result in undesirable tendon translations.

In a more specific, active feedback, form of the invention, sensors are embedded in an enveloping or band-like garment which garment is then positioned over the hand or wrist areas of the user. Information indicating a match between an energy signature (e.g. an acoustic signature) of translational movement of the tendons (snapping) in the carpal tunnel and energy actually generated from the wrist area of a person is used to transmit feedback to a control means, which control means then restricts or changes the operation of the equipment being used so that the user is limited in the ability to continue normal operation with hand use patterns which generate the undesirable tendon snapping.

The invention also includes a method comprising the step of monitoring energy generated within the wrist, and comparing a signature associated with such energy to determine if such signature is indicative of translational movement of the tendons across the carpal tunnel, where such signature has been previously recorded and stored for later use.

Advantages of the invention will be apparent from the following detailed description and the accompanying drawings.

BRIEF DESCRIPTION OF THE DRAWINGS

The invention is described in more detail hereinafter with reference to the accompanying drawings wherein like reference characters refer to the same parts throughout the several views and in which:

FIG. 5 is a diagram showing the elements of an apparatus or method according to the invention.

DESCRIPTION OF THE PREFERRED EMBODIMENT

Figure 1:
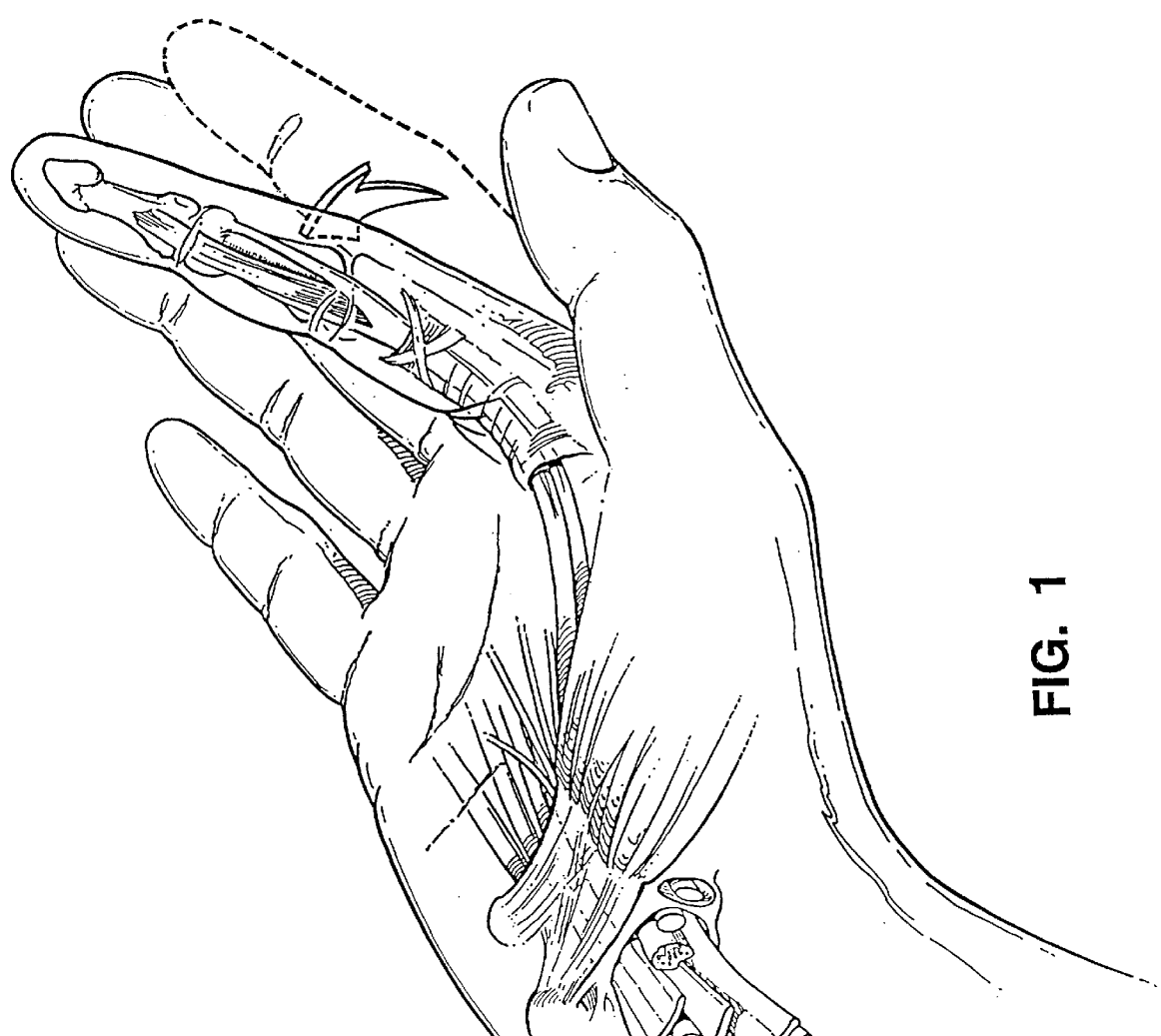
FIG. 1 is a partially cut-away perspective view of a hand showing some of the various tendons in the hand which control finger and thumb movement.

The foundation of the present invention is the recognition that so called idiopathic carpal tunnel syndrome, particularly as it occurs in keyboard operators, is a result of the way in which people use their fingers, hands, wrists, and forearms, referred to as hand use patterns. Typically, many subjects form habits of using the fingers with the distal joint extended so that, for example, the keys on a keyboard are pressed with the palmar aspect of the pulp of the finger, rather than with its palmar-distal tip. This "habit", along with a minimal actuation force requirement of the "modern" computer keyboard, allows the relatively singular contraction of one of the extrinsic muscle tendon units (typically the flexor digitorum sublimis), while leaving other extrinsic muscle tendon units relatively or absolutely relaxed where they pass through the carpal tunnel.

Due to angulation of the tendon as it crosses the wrist, a translational force results in movement of this singular tendon across the carpal tunnel and between the neighboring tendons. This movement produces shear stresses at the interface between adjacent tendons and their associated synovial membranes. In the acute stages, the cyclic shear stress would cause an acute edema formation, and a transient rise in carpal tunnel pressures, with secondary clinical signs and symptoms of carpal tunnel syndrome. Repeated episodes would produce increasing degrees of edema formation and an associated cellular transudate with proteinaceous materials in the interstitial spaces, progressively being converted into inelastic "fibrous tissue", i.e., an evolutionary process of the development of scar formation.

A progressive hypertrophy of tissues is alluded to in a monograph by Dr. Paul W. Brand, "Repetitive Stress on Insensitive Feet, The Pathology and Management of Plantar Ulceration in Neuropathic Feet", U.S. Public Health Service Hospital, Carville, La. He referred to two tests where moderate loads were repetitively placed on rat foot pads. In the first, these repetitive stresses built up an inflammatory state day-by-day until it finally caused an ulceration. In the second test, the same load was applied with 20 percent fewer daily repetitions and rest at weekends, which allowed the feet to pass through the inflammatory phase and move on to a hypertrophy of the tissues without inflammation, which protected the foot from further damage. This hypertrophy is a commonly observed phenomenon in the soft tissues of the body where moderate sheer stresses cause a thickened or callused area without inflammation.

The same process could be visualized in the carpal tunnel as a progressive transformation of the thin elastic synovial membrane, due to sheer stresses, into a more edematous, thickened, and less compliant structure. Pathophysiologically, this would cause an increase in carpal tunnel pressures paralleled by the clinical development of carpal tunnel syndrome and its known signs and symptoms.

At first, it would be a cyclic increase and decrease in carpal tunnel pressure as the edema fluid would accumulate and then dissipate as a function of the level of injury to the synovium. With the persistent shear stresses induced by carpal tunnel tendon instability, the thickening would progressively increase, thereby producing a constant increase in carpal tunnel pressures and an established clinical case of carpal tunnel syndrome.

In order to avoid this process, it is desirable to modify the hand use patterns of persons who may be routinely, but unknowingly, moving their wrists and digits in inappropriate ways. Before such modifications can be made, however, the condition of the tendons in the carpal tunnel must be monitored.

Since the use of keyboards is a common use of the hands which has been associated with CTS, such use can be used as a basis for explaining how monitoring can be achieved.

When a keyboard is to be used, the selection of an appropriate key actuation force can be determined from the anatomical dimensions of the distal joints of the fingers, along with the strength of the flexor digitorum sublimus (FDS) muscle tendon unit as it acts at the proximal interphalangeal (PIP) joint. In terms of carpal tunnel tendons, the individual is mainly using the FDS muscle tendon unit with the intrinsic muscles (flexor digitorum profundus electrically and mechanically silent) to depress a key, keeping the distal interphalangeal (DIP) joints relatively extended. The forces are transmitted through the DIP joints to the pulp at the tip of the distal phalanx, via the DIP joint capsular ligaments and volar plate. The distal and middle phalanx act as one "rigid" structure, with key actuation force provided by a single extrinsic muscle tendon unit, i.e. the flexor digitorum sublimis only.

A simple way to inhibit this undesirable hand use pattern is to require forces greater than the FDS and intrinsic muscles can provide alone, without exceeding the combined capability of the FDS and FDP muscles. The total mechanics in the digits are very complex, but in this case as described above, a simple analysis based on the geometry and FDS tendon forces should be sufficient. L. D. Ketchum from measurements in vivo, estimated the maximum tendon force capability in 40 individuals, as reported in "A clinical study of forces generated by the intrinsic muscles of the index finger and the extrinsic flexor and extensor muscles of the hand", The Journal of Hand Surgery, Nov. 1978, vol. 3, No. 6, pp. 571–578, incorporated herein by reference. He also measured the joint moment arms in 10 fresh frozen cadavers.

The remaining anatomical data for the calculation is described by G. T. Lin in "Functional anatomy of the human digital flexor pulley system", The Journal of Hand Surgery, Nov. 1989 vol. 14A, No. 6, pp. 949956, incorporated herein by reference. Lin measured bone lengths in a radiographic study of 10 hands. These measurements of bone length can be used to approximate the distance from the PIP joint center of rotation to the middle of the pad of the distal phalanx.

The analysis is that of a simple structure with forces creating moments about the PIP joint center of rotation. If a force perpendicular to the axis of the phalanx is assumed, the equation for the key force capability can be derived and is described as follows and is calculated in the table:

Key force = FDS tendon force ×
PIP moment arm/(DP length + MP length)

| Finger | DP length mm | MP length mm | FD moment mm | FDS Force Kg | Key Force Kg |
|---|---|---|---|---|---|
| Index | 18.73 | 24.03 | 8.3 | 6.91 | 1.34 |
| Long | 18.61 | 28.00 | 8.7 | 7.63 | 1.42 |
| Ring | 18.48 | 26.04 | 8.5 | 6.21 | 1.19 |
| Little | 16.85 | 18.57 | 7.4 | 3.73 | 0.78 |

Based on this nominal data, the desired key force for actuation would be in the range of one kilogram. Even though this is an average case, in reality, individuals with lesser or greater strength would find it difficult or impossible to type using the FDS alone with this level of force required. In any case, this analysis shows that calculations can be made which provide guidance as to a specific method of avoiding finger movements which may result in the symptoms associated with CTS. Such guidance is appropriate only where accurate information about what is going on within the carpal tunnel can be collected. Thus, this invention relates to the collection and use of such information, and the active or passive feedback of that information.

By way of further description of the drawings, FIG. 1 illustrates the tendons in the hand which pass through the carpal tunnel within a tendon sheath (ulnar bursa) 10. Tension on the sublimis tendon 12 causes dorsal movement of the tendon and subjects the interposed synovium (i.e., the "tendon sheath") to shear forces which can result in micro trauma.

Figure 2:
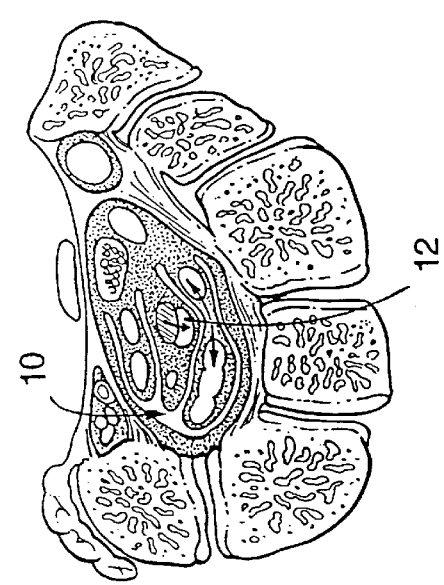
FIG. 2 is a cross-sectional view through the carpal tunnel showing dorsal displacement of the sublimis tendon during its muscle's contraction.
Figures 3, 4:
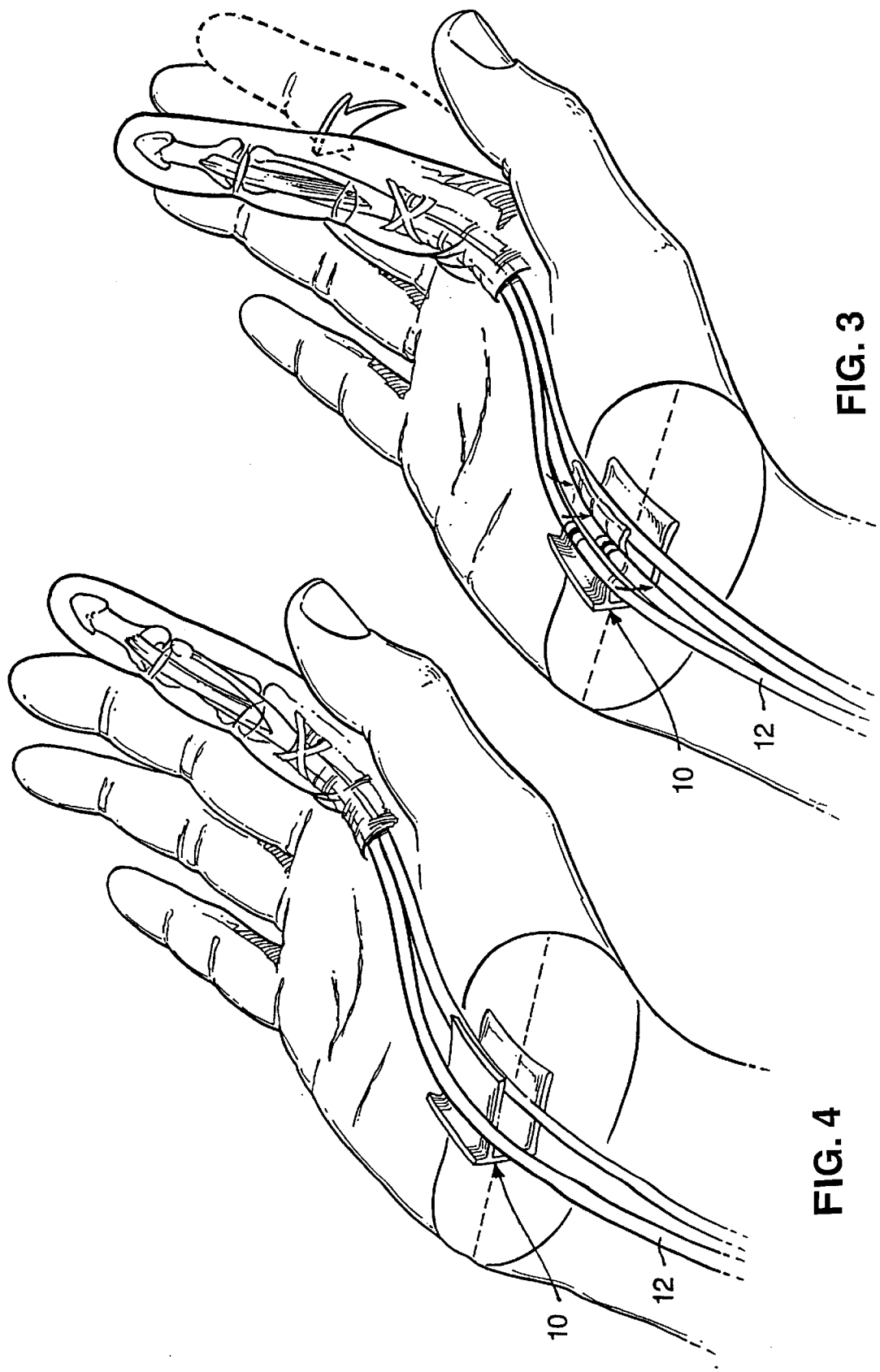
FIGS. 3 and 4 show a sublimis tendon in the hand before and during muscle contraction, respectively.

FIG. 2 is a cross-sectional view through the carpal tunnel showing the manner in which tension on the sublimis tendon 12 causes dorsal movement of the tendon and subjects the tendon synovium (sheath) to shear forces. This phenomenon is also illustrated in FIGS. 3 and 4.

FIG. 5 is a block diagram showing the monitoring apparatus or method of the invention. In FIG. 5, it is shown that data is first obtained via a monitor, using a probe 16. Many types of data collecting probes are well known in the art of gathering data from the body, and any of these which are sensitive enough to collect the energy generated by the interaction of the synovium with the tendons as they translate across the carpal tunnel will be useful in the invention. Typically, vibrations generated would result in the generation of acoustic energy. Where this is the case we have found that, with proper training, a common stethoscope can be used.

As a monitor, any standard data collection device, such as a tape recorder, video camcorder, or computer memory can be used.

Once the data is collected, it may be of interest to subject the data to some analysis, in the sense that it may be necessary to eliminate from the raw data sounds extraneous to those of interest. This is accomplished using hardware or software devices 18, such as filters, spectrum analyzers, and so forth, to analyze and extract the relevant sounds from the raw data.

Integrated data collection, analysis and comparison devices are known for monitoring other sounds generated in the body, most commonly the heart, and these devices may be incorporated into the method or apparatus of the invention. An example of such a device is described in U.S. Pat. No. 5,010,889, which is incorporated herein by reference.

A comparator can then be used to determine if the relevant sounds isolated during data analysis are the same as sounds previously recorded for a given subject. Otherwise, the analyzed or compared data may be used to generate a signal 22 to provide feedback to the subject, or to someone working with the subject. The signal 22 portion of the apparatus or method of the invention can include active means for controlling the hand use patterns of the subject (such as disabling the keyboard of a computer if improper hand use patterns are detected).

EXPERIMENTAL

Previous biomechanical studies (such as that reported by Martin Skie, et. al., in "Carpal tunnel changes and median nerve compression during wrist flexion and extension seen by magnetic resonance imaging", The Journal of Hand Surgery, 1990, Vol. 15A, pgs 934–9) have defined a potential for tension forces, in the carpal tunnel tendons of an angulated wrist, to compress the median nerve against the flexor retinaculum.

A cadaver study was done to examine biomechanical factors that produce instability of the sublimis digital flexor tendons in the carpal tunnel. This study tests the hypothesis that tendon instability created by differential tendon loading can be the initiating cause of "idiopathic" carpal tunnel syndrome (CTS).

When a single sublimus tendon is loaded in excess of its neighboring tendons, that tendon translates around adjacent tendons thereby providing the energy for shear stresses and other cyclic load phenomenon that could lead to synovial thickening and secondary CTS.

Six fresh cadaver specimens were instrumented to simultaneously monitor digital flexor-tendon excursion and wrist-joint angular displacement during arcs of wrist flexion-extension, and radial-ulnar deviation. With each arc of motion, the instantaneous moment arms of each of the carpal tunnel tendons were calculated and recorded. Baseline data defined the moment arms of these tendons at the wrist using identical tension loads in each tendon (85 grams). The experiment was then repeated four times with each sublimis tendon loaded higher than the other 8 tendons (540 gms). Compared to the balanced loads, a reproducible shift in moment arms was demonstrated with each sublimus tendon at the higher loading condition. This shift demonstrated the unstable translation across the tunnel of that sublimus tendon, with a displacement of the other tendons around it.

By repeating the experiment with the fingers in extension, mid flexion, and full flexion, the potential effect of related structures, such as the anatomically linked profundus tendons and the lumbrical muscles, was considered.

The normally thin and compliant synovium of the carpal tunnel is mechanically incapable of assuring a continuous stable relationship between differentially loaded tendons of the carpal tunnel. This data supports the hypothesis that stability of single or multiple carpal tunnel tendons can only be achieved by a continuous synergistic contraction of a host of muscle tendon units orchestrated by the brain. This synergism allows neighboring tendons to provide a stable path for those tendons that are actually performing the instantaneous tasks needed to accomplish a given finger/hand function. Tendon instability accompanying certain common hand use patterns may create tendon translation, with cyclic shear stresses on the interposed synovium, that leads to the edema, fibrosis, and synovial thickening seen in idiopathic CTS. In the use of certain keyed instruments, such as the computer or piano, an individual operator may adopt certain hand use patterns that fail to "recruit" the synergistic muscle contractions necessary to stabilize the motions of each tendon as it performs its function.

The data collected, relevant anatomy, and hand use patterns that may be associated with tendon instabilities indicate that tendon translation can be monitored using any device that will measure the vibrational energy generated by the interaction of the tendons and surrounding tissues (i.e., the synovium and walls of the carpal tunnel) during tendon translation.

In a preferred form, the invention is a method of monitoring the occurrence of such translations. Such monitoring, in its simplest form, can be by listening to the portion of the energy in the range audible to the human ear, even though other frequencies are detectable. A stethoscope can be used to enhance the capability of the listener to identify the particular sound generated by the translation.

In a further form of the invention, any energy generated by the translation, such as acoustic energy, can be monitored by any number of known devices, which devices can then be used to feed the information back to the person being monitored, or to others who need to know, such as a physician, supervisor, or employer. For example, in this form of the invention, a sensitive microphone could be placed on an overlying area of a user's wrist. Sounds generated by tendon translation in the carpal tunnel are then monitored by a device receiving information from the microphone. A signal is generated in the device in response to sounds which indicate tendon translation is occurring, such that the person being monitored is advised that this translation is occurring and can modify the movements of the wrist and hand to eliminate the translating of the tendons. This method can thus be used to allow a user to modify their hand use patterns to eliminate tendon translation within the carpal tunnel. Or at the least, identify those individuals who will be at risk of developing CTS if they continue their hand use patterns without modification.

In an additional form of the invention, the motion of tendons is monitored by means of rapid motion magnetic resonance imaging, commonly referred to as MRI or rapid MRI. This imaging gives a cross-sectional and/or three dimensional view of the internal soft tissues in the body. With proper selection of the plane of the cross section, single or multiple tendons can be viewed as they pass through the carpal tunnel. With pattern recognition software, the translation of a tendon or tendons across the tunnel can be visualized and recorded. This translation can be used to trigger feedback to a control means used for limiting or changing the hand use patterns of the individual being monitored. Similar imaging methods could be utilized such as Computed Tomography (CT), ultrasound, X-ray, infrared, or other frequencies of the electromagnetic spectrum which would penetrate the tissues of the body.

What is claimed is:

1. A method for detecting events related to tendon translation in the carpal tunnel, the method comprising the steps of:

(a) monitoring energy produced by tendon movement resulting in the interaction of tendons and surrounding carnal tunnel structures during hand use; and (b) determining the frequency or amount of said energy and thereby evaluate the presence or absence of snapping of the tendons against the carpal tunnel structures during said hand use.

2. A method in accordance with claim 1, further comprising the step of comparing the characteristics of any such energy to energy characteristics previously recorded.

3. A method in accordance with claim 1, further comprising the step of providing information to or about a person being monitored.

4. A method in accordance with claim 1, further comprising the step of causing a person being monitored to modify hand use patterns to eliminate or reduce the energy produced by said tendon translation.

5. An apparatus for detecting events related to tendon translation in the carpal tunnel, the apparatus comprising:

(a) means for monitoring energy produced by tendon movement resulting in the interaction of tendons and surrounding carpal tunnel structures during hand use; and (b) means for determining the frequency or amount of said energy and thereby evaluate the presence or absence of snapping of the tendons against the carpal tunnel structures during said hand use.

6. An apparatus in accordance with claim 5, further comprising means for comparing the characteristics of any such energy to energy characteristics previously recorded.

7. An apparatus in accordance with claim 5, further comprising means for causing a person being monitored to modify hand use patterns to reduce the amount of said energy.

8. An apparatus in accordance with claim 5, further comprising multiple means for detecting energy, where a phase shift of signals from various detectors is used to determine an originating location of said energy within tissues in the wrist or hand.

9. An apparatus in accordance with claim 5, further comprising detectors mounted on finger nails or tips of the fingers on a hand in close proximity to bony structures of fingers to which tendons of each digit are attached, to detect energy generated by the movement of each tendon.

10. The method of claim 1 wherein the step of monitoring includes the use of computed tomography, ultrasound, X-ray, infrared, magnetic resonance or other frequencies of the electromagnetic spectrum which would penetrate the tissues of the body.

11. The apparatus of claim 5 wherein said means for monitoring includes a monitoring device using computed tomography, ultrasound, X-ray, infrared, magnetic resonance or other frequencies of the electromagnetic spectrum which would penetrate the tissues of the body.

12. An apparatus for detecting events related to tendon translation in the carpal tunnel, the apparatus comprising:

(a) ultrasound means for monitoring energy generated by the interaction of tendons with the synovium in the carpal tunnel during hand use; and (b) means for determining the frequency or amount of said energy.

13. A method for detecting events related to tendon translation in the carpal tunnel, the method comprising the steps of:

(a) monitoring energy produced by tendon movement resulting in the interaction of tendons and surrounding carpal tunnel structures including soft tissue during hand use; and (b) determining the frequency or amount of said energy and thereby evaluate the elastic compliance of said soft tissue.

14. A method in accordance with claim 13 wherein said tissue includes the synovium.

15. A method in accordance with claim 13 wherein the elastic compliance is defined by edema.

16. A method in accordance with claim 13 wherein the elastic compliance is defined by the development of scar formation.

17. A method in accordance with claim 13 wherein the elastic compliance is defined by fibrous tissue.

18. A method in accordance with claim 13 wherein the elastic compliance is defined by cellular transudate with proteinaceous materials.

19. A method in accordance with claim 13 wherein the elastic compliance is defined by thickened synovium.

20. A method in accordance with claim 13 wherein the elastic compliance is defined by soft tissue hypertrophy.

21. The method of claim 13 wherein said monitoring step includes the use of computed tomography, ultrasound, x-ray, infrared, magnetic resonance or other frequencies of the electromagnetic spectrum which would penetrate the tissues of the body.

22. An apparatus for detecting events related to tendon translation in the carpal tunnel, the apparatus comprising:

(a) means for monitoring energy produced by tendon movement resulting in the interaction of tendons and surrounding carpal tunnel structures including soft tissue during hand use; and (b) means for determining the frequency or amount of said energy and thereby evaluate the elastic compliance of said soft tissue.

23. An apparatus in accordance with claim 22 wherein said tissue includes the synovium.

24. An apparatus in accordance with claim 22 wherein the elastic compliance is defined by edema.

25. An apparatus in accordance with claim 22 wherein the elastic compliance is defined by the development of scar formation.

26. An apparatus in accordance with claim 22 wherein the elastic compliance is defined by fibrous tissue.

27. An apparatus in accordance with claim 22 wherein the elastic compliance is defined by cellular transudate with proteinaceous materials.

28. An apparatus in accordance with claim 22 wherein the elastic compliance is defined by thickened synovium.

29. An apparatus in accordance with claim 22 wherein the elastic compliance is defined by soft tissue hypertrophy.

30. The apparatus of claim 22 wherein said means for monitoring includes a monitoring device using computed tomography, ultrasound, x-ray, infrared, magnetic resonance or other frequencies of the electromagnetic spectrum which would penetrate the tissues of the body.

* * * * *